(12) United States Patent
Vahala et al.

(10) Patent No.: US 10,307,616 B2
(45) Date of Patent: Jun. 4, 2019

(54) MEDICAL APPARATUS WITH A RADIATION THERAPY DEVICE AND A RADIATION DETECTION SYSTEM

(71) Applicant: KONINKLIJKE PHILIPS N.V., Eindhoven (NL)

(72) Inventors: Erkki Tapani Vahala, Hyvinkaa (FI); Thomas Erik Amthor, Hamburg (DE); Peter Forthmann, Latham, NY (US)

(73) Assignee: Koninklijke Philips, N.V., Eindhoven (NL)

( * ) Notice: Subject to any disclaimer, the term of this patent is extended or adjusted under 35 U.S.C. 154(b) by 442 days.

(21) Appl. No.: 15/029,343

(22) PCT Filed: Oct. 8, 2014

(86) PCT No.: PCT/EP2014/071485
§ 371 (c)(1),
(2) Date: Apr. 14, 2016

(87) PCT Pub. No.: WO2015/055473
PCT Pub. Date: Apr. 23, 2015

(65) Prior Publication Data
US 2016/0256712 A1 Sep. 8, 2016

(30) Foreign Application Priority Data

Oct. 17, 2013 (EP) ..................................... 13189072

(51) Int. Cl.
*A61N 5/10* (2006.01)
*A61B 90/00* (2016.01)
(52) U.S. Cl.
CPC ......... *A61N 5/1049* (2013.01); *A61N 5/1038* (2013.01); *A61N 5/1039* (2013.01);
(Continued)

(58) Field of Classification Search
CPC ........................................ A61N 5/103–5/1084
See application file for complete search history.

(56) References Cited

U.S. PATENT DOCUMENTS 6,385,286 B1 7/2002 Fitchard et al.
8,467,497 B2 6/2013 Lu et al.
(Continued)

FOREIGN PATENT DOCUMENTS

EP 2359905 A1 8/2011
JP 2009160309 A 7/2009
(Continued)

OTHER PUBLICATIONS

Raaymakers et al "Integrated Megavoltage Portal Imaging with a 1.5 T MRI Linac" Phys. Med. Biol. 56 (2011) N207-N214.

*Primary Examiner* — Thaddeus B Cox

(57) ABSTRACT

A medical apparatus (100, 300, 400, 800) includes a magnetic resonance imaging system (104), a radiation therapy device (102) having a gantry (106) and a radiation source (110). A radiation detection system (102) measures radiation detection data (174) descriptive of a path and intensity of a radiation beam at an intersection of the radiation beam with at least one surface (144, 144', 144") surrounding the subject using at least one radiation detector (144, 144', 144"). Execution of machine readable instructions causes a processor controlling the medical apparatus to: receive (200) a treatment plan (168), acquire (202) magnetic resonance data (164) from the imaging zone using the magnetic resonance imaging system, generate (204) radiation therapy device control commands (172) using the magnetic resonance data and the treatment plan, irradiate (206) the target zone by controlling the radiation therapy device using the radiation therapy device control commands, measure (208) the radiation detection data during irradiation, and determine a time dependent radiation beam path (176) and a time dependent radiation beam intensity (178) using the radiation detection data.

15 Claims, 9 Drawing Sheets

(52) U.S. Cl.
CPC ......... *A61N 5/1047* (2013.01); *A61N 5/1067* (2013.01); *A61N 5/1075* (2013.01); *A61N 5/1081* (2013.01); *A61B 2090/374* (2016.02); *A61B 2090/3954* (2016.02); *A61N 2005/1052* (2013.01); *A61N 2005/1054* (2013.01); *A61N 2005/1055* (2013.01); *A61N 2005/1059* (2013.01)

(56) References Cited

U.S. PATENT DOCUMENTS

| | | | |
|---|---|---|---|
| 2008/0284428 A1* | 11/2008 | Fiedler | G01R 33/28 324/307 |
| 2010/0316259 A1 | 12/2010 | Liu et al. | |
| 2013/0261430 A1* | 10/2013 | Uhlemann | A61N 5/1067 600/411 |
| 2013/0267830 A1 | 10/2013 | Ojha et al. | |
| 2014/0021358 A1* | 1/2014 | Wieringa | G01T 1/1603 250/366 |
| 2014/0275939 A1* | 9/2014 | Mitteldorf | A61B 6/46 600/407 |
| 2016/0008630 A1 | 1/2016 | Ranganathan et al. | |

FOREIGN PATENT DOCUMENTS

| | | | |
|---|---|---|---|
| WO | 2006113323 A2 | 10/2006 | |
| WO | 2006130659 A2 | 12/2006 | |
| WO | 2013001399 A2 | 1/2013 | |

\* cited by examiner

FIG. 10
FIG. 11
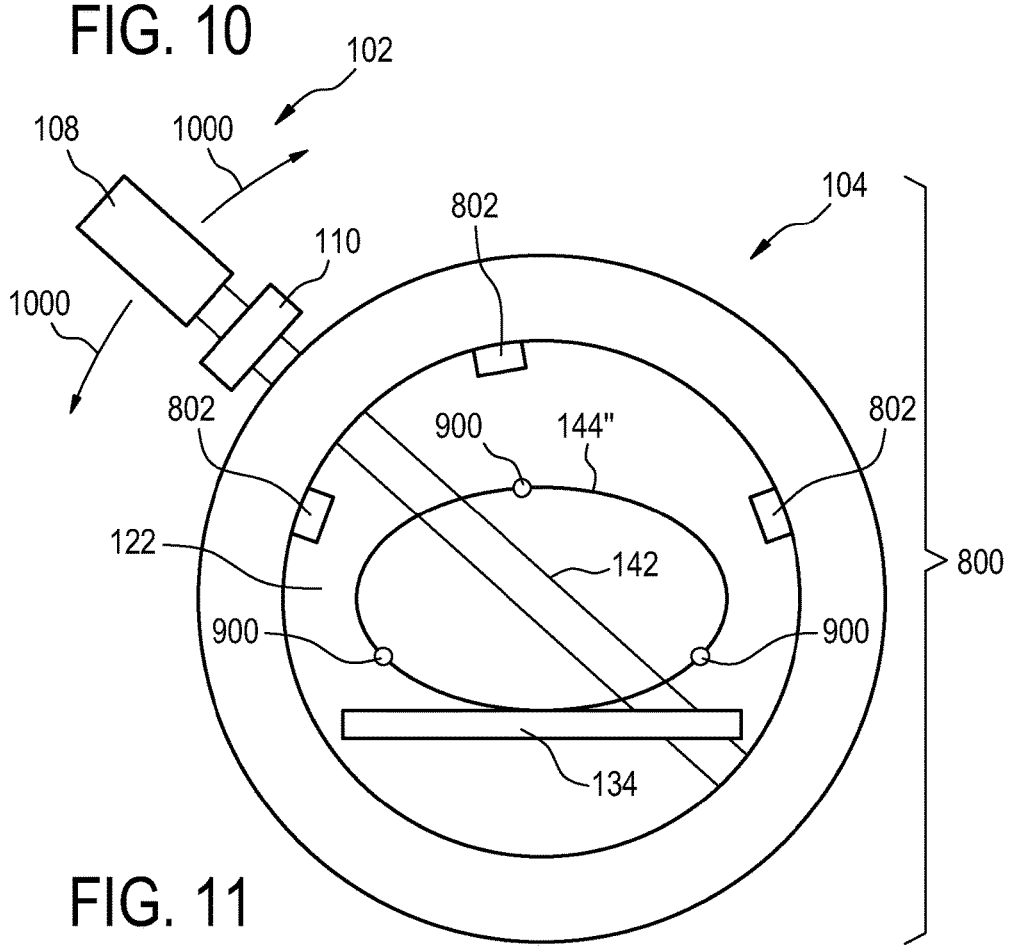
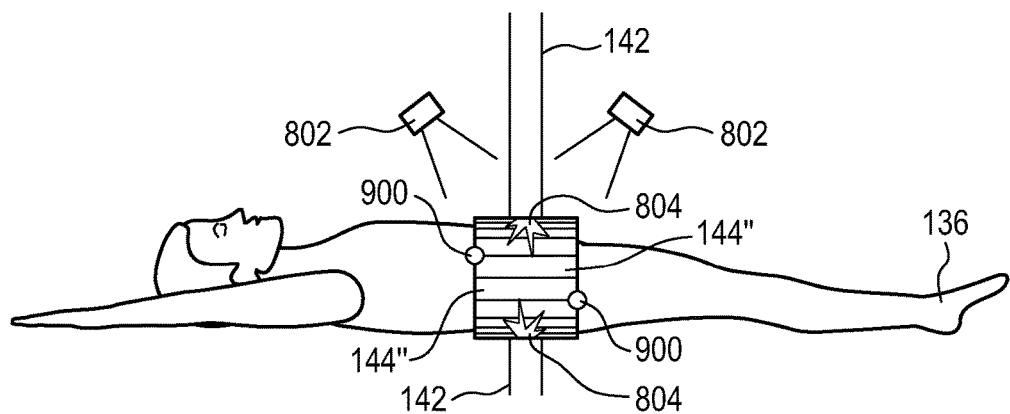

MEDICAL APPARATUS WITH A RADIATION THERAPY DEVICE AND A RADIATION DETECTION SYSTEM

CROSS REFERENCE TO RELATED APPLICATIONS

This application is a U.S. national phase application of International Application No. PCT/EP2014/071485, filed on Oct. 8, 2014, which claims the benefit of EP Application Serial No. 13189072.5 filed on Oct. 17, 2013 and is incorporated herein by reference.

TECHNICAL FIELD

The invention relates to radiation therapy devices, in particular to magnetic resonance guidance of radiation therapy devices.

BACKGROUND OF THE INVENTION

Integration of MR (Magnetic Resonance) imaging and Linear Accelerators (LINAC) opens new horizons in Radiotherapy by improved lesion targeting, especially for moving organs. In a practical implementation proposal, the LINAC rotates around the subject to hit the gross target volume (GTV) and clinical target volume (CTV) from multiple angles while minimizing the radiation exposure for surrounding tissues. The combination of magnetic resonance apparatuses and LINAC radiotherapy sources is known.

The journal article Raaymakers et. al., "Integrated megavoltage portal imaging with a 1.5 T MRI linac," Phys. Med. Biol. 56 (2011) N207-N214, doi:10.1088/0031-9155/56/19/N01 discloses the combination of a 1.5T MRI LINAC with a megavoltage portal imager.

EP2359905A1 describes a radiotherapy and imaging apparatus. The radiotherapy and imaging apparatus comprises a radiation detector, which can be used for QA and in-vivo dosimetry. The detector is positioned outside the magnetic coils mounted to the gantry, aligned with the radiation beam exit. It therefore has a fixed position relative to the radiation source.

US2010/0316259A1 describes a method for real-time 3D tracking of anatomical position during radiation therapy. To this end, during arc radiotherapy treatment, tomosynthetic images from projection images of an MV treatment beam are reconstructed.

SUMMARY OF THE INVENTION

The invention provides for a medical apparatus, a computer program product, and a method in the independent claims. Embodiments are given in the dependent claims.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins by the antenna of a Magnetic resonance apparatus during a magnetic resonance imaging scan. Magnetic resonance data is an example of medical image data. A Magnetic Resonance Imaging (MRI) image is defined herein as being the reconstructed two or three dimensional visualization of anatomic data contained within the magnetic resonance imaging data. This visualization can be performed using a computer.

In one aspect the invention provides for a medical apparatus. The medical apparatus comprises a magnetic resonance imaging system for acquiring magnetic resonance data from a subject within an imaging zone. The magnetic resonance imaging system comprises a main magnet for generating a magnetic field with a main field region. The imaging zone is within the main field region. A 'main field region' as used herein encompasses a region where the main magnet is operable for generating a magnetic field that is large compared to the ambient magnetic field of the earth. For example the main field region may be any region where the magnetic field is greater than, or approaches to, for example: 0.25 T, 0.5 T, or 1 Tesla. In a cylindrical magnet the main field region roughly corresponds to the bore of the magnet. As a result in a cylindrical magnet the "main field region" can be replaced by "within the bore of the magnet" and/or by "within a volume defined by the gradient coils."

The medical apparatus further comprises a radiation therapy device. The radiation therapy device comprises a gantry and a radiation source. The gantry is operable for rotating the radiation source about a rotational axis. The radiation source is operable for generating a radiation beam directed at the rotation of axis. The radiation source is operable for directing the radiation beam towards a target volume. The rotational axis intersects the target volume. The target volume is within the imaging zone.

The medical apparatus further comprises a radiation detection system covering a substantial part of the rotation of the gantry and operable for measuring radiation detection data descriptive of the path and intensity of the radiation beam at the intersection of the radiation beam with at least one surface surrounding the subject using at least one radiation detector. The radiation detector may be placed on a portion of the surface surrounding the subject such that the radiation detector can directly measure the location and the intensity of the radiation beam. The at least one radiation detector is operable for being placed within the main field region.

The medical apparatus further comprises a subject support operable for supporting the subject. The subject support may support at least a portion of the subject within the imaging zone.

The medical apparatus further comprises a memory for storing machine-executable instructions. The medical apparatus further comprises a processor for controlling the medical apparatus.

Execution of the machine-executable instructions causes the processor to receive a treatment plan descriptive of the radiation of a target zone within the subject. The treatment plan may also contain other data such as the location of the target zone relative to other anatomical landmarks or portions of the subject. The subject support is further operable for positioning the target volume within the target zone. Execution of the machine-executable instructions further cause the processor to acquire planning magnetic resonance data from the imaging zone using the magnetic resonance imaging system. Planning magnetic resonance data as used herein encompasses magnetic resonance data. The planning magnetic resonance data may be used for instance for reconstructing an image which may be used to register the coordinate system of the medical apparatus with anatomical landmarks or other positions indicated on the treatment plan. This may enable the identification of the target zone within the subject.

Execution of the machine-executable instructions further causes the processor to generate radiation therapy device control commands using the planning magnetic resonance data and the treatment plan. The radiation therapy device control commands are control or commands which enable the processor to control the operation and function of the radiation therapy device. The radiation therapy device control commands are in other words commands which are operable to cause the radiation therapy device to irradiate the target zone according to the treatment plan. For instance a magnetic resonance image reconstructed from the planning magnetic resonance data may be registered to the treatment plan. Execution of the instructions further causes the processor to irradiate the target zone by controlling the radiation therapy device using the radiation therapy device control commands. The execution of these commands cause the execution of the radiation therapy device control commands by the radiation therapy device.

Execution of the instructions further causes the processor to measure the radiation detection data using the radiation detection system. This is performed during at least a portion of the time when the target zone is irradiated using the radiation therapy device. Execution of the instructions further causes the processor to determine a time-dependent radiation beam path and a time-dependent radiation beam intensity using the radiation detection data. The time-dependent radiation beam path is descriptive of the path of the radiation beam through the subject as a function of time. The time-dependent radiation beam intensity is descriptive of the intensity of the radiation beam in the subject as a function of time. Placing one or two radiation detectors which are able to measure the spatially dependent intensity of radiation may be used to infer the radiation beam path and also the radiation beam intensity as a function of time. For instance if a radiation detector was used to measure the radiation path and intensity going into and out of the subject the path through the subject could be inferred.

In some examples the magnetic resonance imaging system may even acquire magnetic resonance data which is used to build a radiation beam attenuation model. For instance the concentration of boney and fatty and water-based tissue can be measured with the magnetic resonance imaging system. The planning magnetic resonance data may for instance be used to build up an attenuation model which can then be used in conjunction with the radiation detection data to accurately model the intensity and path of the radiation as it passes through the subject.

This embodiment may be beneficial because it may enable accurate determination of the path and intensity of radiation through a subject. This may enable more accurate determination of a three-dimensional dose within the subject and it may also enable more accurate control of the irradiation of the target zone.

In another embodiment execution of the instructions further causes the processor to calculate a spatially dependent radiation dose of the subject using the time-dependent radiation beam path and the time-dependent radiation beam intensity using the radiation detection data. This embodiment may be beneficial because it may enable more accurate determination of the radiation dose to the subject. In some examples the planning magnetic resonance data may be used to construct a model of how the radiation is absorbed by the subject. This may also enable even more accurate calculation of the spatially dependent radiation dose of the subject.

In another embodiment execution of the instructions further causes the processor to calculate a three-dimensional radiation path through the subject using the time-dependent radiation beam path and the time-dependent radiation beam intensity using the radiation detection data. The measurement of the radiation detection data may be measured and processed in real time. For instance the data may then be used to calculate the beam path in intensity as the irradiation is being performed. This may enable more accurate control of the radiation therapy device. Also as mentioned before, the planning magnetic resonance data may for instance be used to make an absorption model for more accurately modeling the time-dependent radiation beam path and the time-dependent radiation beam intensity.

In another embodiment execution of the instructions further causes the processor to modify the radiation therapy device control commands using the time-dependent radiation beam path, the time-dependent radiation beam intensity, the planning magnetic resonance data, and the treatment plan. For instance the treatment plan has the desired irradiation dose in terms of the subject's anatomy. The planning magnetic resonance data may be used for registering to the treatment plan and also for making a radiation beam absorption model of the subject. The time-dependent radiation beam path and the time-dependent radiation beam intensity may then be used with the data from the planning magnetic resonance data and the treatment plan to then more accurately control the radiation therapy device. This may enable more accurate irradiation of the target zone.

In another embodiment the medical apparatus comprises the radiation detector. The radiation detector comprises an array of solid state radiation detectors. A solid state radiation detector as used herein encompasses a radiation detector in which a semi-conductor material which detects radiation by detecting a pulse of current which develops across a p-n junction. The use of an array of the solid state radiation detectors enables the spatially and temporally dependent measuring of the location of the radiation beam and also its intensity.

In another embodiment the solid state radiation detectors are arranged in a pseudo random pattern in the array. By arranging the radiation detectors in a pseudo random pattern they may have less effect on the magnetic resonance imaging measurements.

In another embodiment the magnetic resonance imaging system comprises a body coil for measuring the magnetic resonance data and/or transmitting radio-frequency power for performing magnetic resonance imaging. That is to say the body coil may be a transceiver coil, a receiver coil, or a transmit coil operable for performing magnetic resonance imaging. The body coil comprises a radio-frequency shield. The radio-frequency shield comprises a radiation detector. The radio-frequency shield is placed between the elements or antenna segments of the body coil and the coils of the magnet. This may prevent any radio-frequency signals which are generated from affecting the magnetic field gradients electronics and/or the main magnet, and may prevent the magnet from affecting the Q-value and tuning of the body coil. Very typically the radio-frequency shield has breaks in it to allow the time varying magnetic field from the gradient field coils to penetrate it without creating eddy currents. The metal segments may have a pseudo random pattern so as not to have a large effect on the magnetic resonance imaging. In one example the radiation detectors may be integrated into the pattern in the radio-frequency shield.

In another embodiment, the radiation detectors are placed outside the RF-shield of the body coil, but still inside the gradient coils, so that only eddy current gaps are needed and RF interference from the body coil can be neglected.

In another embodiment, the radiation detectors are placed outside the gradient coils, but within the main magnetic field coils.

In another embodiment the radiation detection system further comprises multiple cameras attached to the magnet and directed towards the imaging zone. The memory further contains camera orientation data descriptive of the location, orientation of the multiple cameras relative to the magnet. The radiation detector comprises at least one scintillator film. The at least one scintillator film is operable to emit light of a predetermined frequency spectrum in response to being irradiated by the radiation beam. The scintillator film may for instance be a plastic or flexible film which has a scintillator material. Depending upon the type of radiation beam a scintillator film may be readily available from a commercial manufacturer. The radiation detector is operable to be placed within the imaging zone.

The at least one scintillator film comprises multiple magnetic resonance imaging fiducial markers. The at least one scintillator film comprises optical position markers. The magnetic resonance imaging fiducial markers may be detected in a magnetic resonance image. This enables the position of the at least one scintillator film and its scintillating surface to be registered within the coordinate system of the medical apparatus. The at least one scintillator film comprises optical position markers which also serve the same function with the multiple cameras. For instance a series of machine-readable marks or markings may be placed on the scintillator film to determine the location of the surface of the scintillator film. The same cameras can then be used also to measure light emissions by the scintillators. Essentially the multiple cameras are used to determine the location of the surfaces with respect to the cameras and also to measure the light emissions from the surface.

Execution of the machine-executable instructions further causes the processor to identify the location of the fiducial markers in the planning magnetic resonance data. Execution of the instructions further causes the processor to measure initial images of the at least one scintillator film with the multiple cameras. Execution of the instructions further causes the processor to identify the location of the at least one surface surrounding the subject by identifying the location of the optical position markers in the initial images and using the location of the fiducial markers. This may be particularly beneficial because the same surface has had its position identified using the magnetic resonance imaging system and also with the scintillator system. This data may be used when the radiation beam is scintillating to compare the coordinate systems of the magnetic resonance imaging system and the radiation therapy device. Execution of the machine-executable instructions further causes the processor to acquire the radiation detection data by detecting the light of the predetermined frequency spectrum during irradiation of the target zone.

In another embodiment the medical apparatus further comprises the radiation detector.

In another embodiment the medical apparatus further comprises a subject support with a transparent portion. A portion of the multiple cameras are operable for observing the at least one scintillator film through the transparent portion. This embodiment may be beneficial because the multiple cameras can be used to detect the path of the radiation at a surface which the subject is lying on is resting upon the subject support.

In another embodiment the at least one scintillator film is operable to be wrapped around the subject. For instance the at least one scintillator film may be flexible. This may be beneficial because it may be easy to put the scintillator around the subject then.

In another embodiment the at least one scintillator film is operable to be attached to a garment. For instance the scintillator film may comprise a garment to which the scintillator film is attached. The scintillator film may be for instance plates which are pinned or attached using other removable attachment to a garment.

In another embodiment the radiation therapy device is a LINAC system.

In another embodiment the radiation therapy device is an X-ray system.

In another embodiment the radiation therapy device is a charged particle therapy system which is operable for radiating charged particles such as neutrons, protons, or atomic nuclei at the subject.

In another embodiment the radiation therapy device is a gamma radiation therapy system. For instance the radiation therapy device may be a so-called gamma knife.

In another aspect the invention provides for a computer program product comprising machine-executable instructions for execution by a processor controlling the medical apparatus. The medical apparatus comprises a magnetic resonance imaging system for acquiring magnetic resonance data from a subject within an imaging zone. The magnetic resonance imaging system comprises a main magnet for generating a magnetic field and the magnet is operable for generating a main field region. The imaging zone is within the main field region. The medical apparatus further comprises a radiation therapy device comprising a gantry and a radiation source. The gantry is operable for rotating the radiation source about a rotational axis.

The radiation source is operable for generating a radiation beam directed at the rotational axis. The radiation source is operable for directing the radiation beam towards a target volume. The rotational axis intersects the target volume. The target volume is within the imaging zone. The medical apparatus further comprises a radiation detection system operable for measuring radiation detection data descriptive of the path and intensity of the radiation beam at the intersection of the radiation beam with at least one surface surrounding the subject and using at least one radiation detector. The at least one radiation detector is operable for being placed within the main field region. The medical apparatus further comprises a subject support operable for supporting the subject. Execution of the instructions causes the processor to receive a treatment plan descriptive of the irradiation of a target zone within the subject. The medical apparatus is further operable for positioning the target volume within the target zone.

Execution of the instructions further causes the processor to acquire planning magnetic resonance data from the imaging zone using the magnetic resonance imaging system. Execution of the instructions further causes the processor to generate radiation therapy device control commands using the planning magnetic resonance data and the treatment plan. Execution of the instructions further causes the processor to irradiate the target zone by controlling the radiation therapy device using the radiation therapy device control commands. Execution of the instructions further causes the processor to measure the radiation detection data using the radiation detection system while the target zone is being irradiated. Execution of the instructions further causes the processor to determine a time-dependent radiation beam path and a time-dependent radiation beam intensity using the radiation detection data. The time-dependent radiation beam path is descriptive of path of the radiation beam through the subject as a function of time. The time-dependent radiation beam intensity is descriptive of the intensity of the radiation beam in the subject as a function of time.

In another aspect the invention provides for a method of operating the medical apparatus. The medical apparatus comprises a magnetic resonance imaging system for acquiring magnetic resonance data from a subject within an imaging zone. The magnetic resonance imaging system comprises a main magnet for generating a magnetic field with a main field region. The imaging zone is within the main field region. The medical apparatus further comprises a radiation therapy device comprising a gantry and a radiation source. The gantry is operable for rotating the radiation source about a rotational axis. The radiation source is operable for generating a radiation beam directed at the rotational axis. The radiation source is operable for directing the radiation beam towards a target volume. The rotational axis intersects the target volume. The target volume is within the imaging zone. The medical apparatus further comprises a radiation detection system operable for measuring radiation detection data descriptive of the path and intensity of the radiation beam at the intersection of the radiation beam with at least one surface surrounding the subject using at least one radiation detector. The at least one radiation detector is operable for being placed within the main field region. The medical apparatus further comprises a subject support operable for supporting the subject.

The method comprises the step of receiving a treatment plan descriptive of the irradiation of the target zone within the subject. The subject support is further operable for positioning the target volume within the target zone. The method further comprises the step of acquiring planning magnetic resonance data from the imaging zone using the magnetic resonance imaging system. The method further comprises the step of generating radiation therapy device control commands using the planning magnetic resonance data and the treatment plan. The method further comprises the step of eradiating the target zone by controlling the radiation therapy device using the radiation therapy device control commands. The method further comprises the step of measuring the radiation detection data using the radiation detection system during irradiation of the target zone.

The method further comprises the step of determining a time-dependent radiation beam path and a time-dependent radiation beam intensity using the radiation detection data. The time-dependent radiation beam path is descriptive of the path of the radiation beam through the subject as a function of time. The time-dependent radiation beam intensity is descriptive of the intensity of the radiation beam in the subject as a function of time.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which:

FIG. 10 illustrates a view of the medical apparatus illustrated in FIG. 8; and

FIG. 11 illustrates a further view of the medical apparatus illustrated in FIG. 8.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
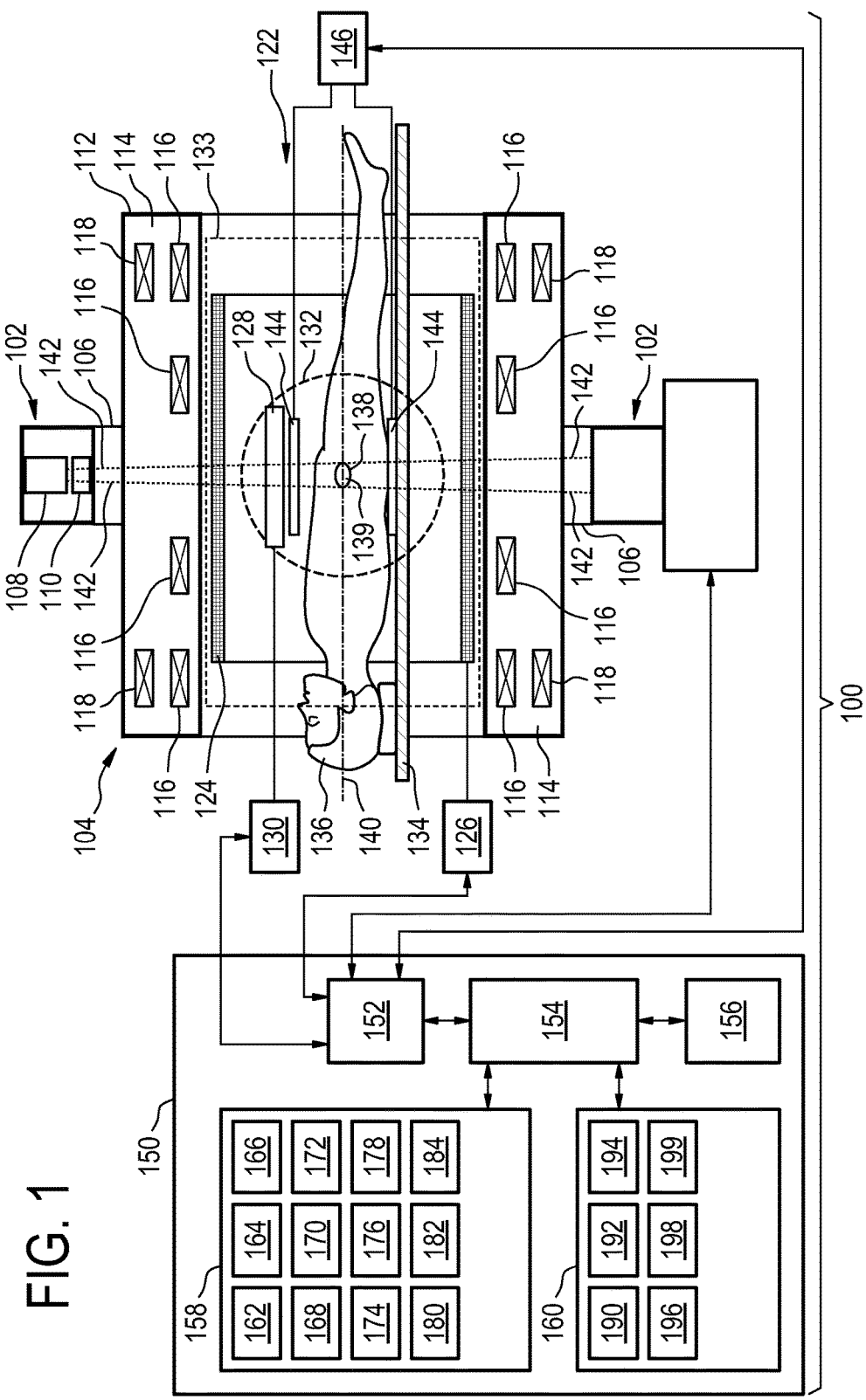
FIG. 1 illustrates an example of a medical apparatus.

FIG. 1 shows an example of a medical apparatus 100. The medical apparatus 100 comprises a radiation therapy device 102 and a magnetic resonance imaging system 104. The radiation therapy device 102 comprises a gantry 106 and a radiotherapy source 108. The gantry 106 is for rotating the radiotherapy source 108 about an axis of gantry rotation or rotational axis 140. Adjacent to the radiotherapy source 108 is a collimator 110. The magnetic resonance imaging system 104 comprises a superconducting magnet 112.

It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore of the cylindrical magnet there is an imaging zone where the magnetic field is strong and uniform enough to perform magnetic resonance imaging.

The magnet 112 shown in this embodiment is a standard cylindrical superconducting magnet. The magnet 112 has a cryostat 114 with superconducting coils within it 116. There are also superconducting shield coils 118 within the cryostat also. The magnet 112 has a bore 122.

Within the bore of the magnet is a magnetic field gradient coil 124 for acquisition of magnetic resonance data to spatially encode magnetic spins within an imaging zone of the magnet. The magnetic field gradient coil 124 is connected to a magnetic field gradient coil power supply 126. The magnetic field gradient coil 124 is intended to be representative, to allow radiation to pass through without being attenuated it will normally be a split-coil design. Typically magnetic field gradient coils contain three separate sets of coils for spatially encoding in three orthogonal spatial directions. The magnetic field gradient power supply 126 supplies current to the magnetic field gradient coils. The current supplied to the magnetic field coils is controlled as a function of time and may be ramped or pulsed.

There is a radio frequency coil 128 connected to a transceiver 130. The radio frequency coil 128 is adjacent to an imaging zone 132 of the magnet 112. The imaging zone 132 has a region of high magnetic field and homogeneity which is sufficient for performing magnetic resonance imaging. The imaging zone 132 is located within the main field region 133. The main field region is also a region of high magnetic field, but not all of the main field region has a magnetic field uniform enough to perform magnetic resonance imaging.

The radio frequency coil 128 may is for manipulating the orientations of magnetic spins within the imaging zone and for receiving radio transmissions from spins also within the imaging zone. The radio frequency coil 128 may also be referred to as an antenna or channel. The radio frequency coil 128 may contain multiple coil elements. The radio frequency antenna may also be referred to as a channel.

The radio frequency coil 128 and radio frequency transceiver 130 may be replaced by separate transmit and receive coils and a separate transmitter and receiver. It is understood that the radio frequency coil and the radio frequency transceiver are representative. The radio frequency antenna is intended to also represent a dedicated transmit antenna and a dedicated receive antenna. Likewise the transceiver may also represent a separate transmitter and receivers.

Also within the bore of the magnet 122 is a subject support 134 for supporting a subject 136. The subject support 134 may be positioned by a mechanical positioning system, which is not shown in this figure. Within the subject 136 there is a target zone 138. The axis of gantry rotation 140 is coaxial in this particular embodiment with the cylindrical axis of the magnet 112. The radiation source 108 is aimed at the axis of rotation 140 such that the radiation source has a target volume about the axis of the rotation 140.

The subject support 134 has been positioned such that the target zone 138 lies on the axis 140 of gantry rotation. The radiation source 108 is shown as generating a radiation beam 4142 which passes through the collimator 110 and through the target zone 138. As the radiation source 108 is rotated about the axis 140 the target zone 138 will always be targeted by the radiation beam 142. The radiation beam 142 passes through the cryostat 114 of the magnet. The magnetic field gradient coil may have a gap which separate the magnetic field gradient coil into two sections. If present, this gap reduces attenuation of the radiation beam 142 by the magnetic field gradient coil 124. In some embodiments the radio frequency coil 128 may also have gaps or be separated to reduce attenuation of the radiation beam 142.

Within the bore 122 of the magnet 112 there is the imaging zone 132. Surrounding the imaging zone 132 is the main field region 133. The main field region 133 still has a relatively high magnetic field but it is not as uniform as it is within the imaging zone 132. The radiation beam 142 is shown as being focused at the rotational axis 140. About the point where the gantry 106 rotates is target volume 139. The target zone 138 of the subject 136 has been moved such that the target zone 138 and the target volume 139 are in the identical location. There are two radiation detectors 144 on either side of the beam 142 before it enters the subject 136 and after it exits the subject 136. These detectors 144 are intended to be representative of a radiation detector which can measure the spatial dependence and intensity of the radiation beam 142. The radiation detectors 144 are shown as being connected to a radiation detection system 146. The radiation detection system 146 is also intended to be representative. For example in the case of a semi-conductor array of detectors this would be an electrical connection that allows the radiation detection system 146 to measure the radiation measured by the individual semi-conductor radiation sensors. However, this 146 is also intended to represent other sorts of systems for instance a camera or optical system for detecting emission by scintillators.

The transceiver 130, the magnetic field gradient coil power supply 126, and the radiation detection system 146, are all shown as being connected to a hardware interface 152 of a computer system 150. The computer system 150 is shown as further comprising a processor 154 for executing machine executable instructions and for controlling the operation and function of the therapeutic apparatus. The hardware interface 152 enables the processor 154 to interact with and control the medical apparatus 100. The processor 154 is shown as further being connected to a user interface 156, computer storage 158, and computer memory 160.

The computer storage 158 is shown as containing a pulse sequence 162. The pulse sequence 162 either contains data which can be converted into commands or commands themselves which can be used for controlling the magnetic resonance imaging system 104 for acquiring magnetic resonance data. The computer storage 158 is further shown as containing magnetic resonance data 164 which has been acquired with a pulse sequence 162. Magnetic resonance data 164 contains magnetic resonance data for imaging at least the area of the subject 136 which has been intersected by the radiation beam 142 and possibly surrounding areas of the subject 136 within the imaging zone 132. The computer storage 158 is shown as containing magnetic resonance image 166 that was reconstructed from the magnetic resonance data 164.

The computer storage 158 is further shown as containing a treatment plan 168. The treatment plan 168 may contain such data as descriptive of the desired radiation dose to the target zone 138 and also data concerning the anatomical references within a subject 136. For instance the treatment plan 168 may contain data which enables an image processing module to register data or landmarks within the treatment plan 168 to the magnetic resonance image 166. The computer storage 158 is shown as further containing a registration between the image 166 and the treatment plan 168. The computer storage 158 is further shown as containing radiation therapy device control commands 172 which are operable for causing the patient therapy device 102 to irradiate the target volume 139. The computer storage 158 is further shown as containing radiation detection data 174 that was acquired by the radiation detectors 144.

The radiation detectors essentially define a surface around the subject 136 which the radiation beam 142 passes through. The computer storage is further shown as containing a time-dependent radiation beam path 176 and a time-dependent radiation beam intensity 178 that was derived from or calculated from the radiation detection data 174. The computer storage 158 is further shown as containing a radiation absorption model of the subject 180. The radiation absorption model 180 may be for instance generated using the magnetic resonance image 166. In some instances the magnetic resonance image 166 may contain information about the different tissue types along the path of the radiation beam 142. This may enable in conjunction with the time-dependent radiation beam path 176 and time-dependent radiation beam intensity 178 to calculate a spatially dependent radiation dose 182 or three-dimensional radiation path 184 through the subject 136. Both the radiation dose 182 and the radiation path 184 are shown as being stored within the computer storage 158.

The computer memory 160 is shown as containing a control module 190. The control module 190 contains computer-executable code which enables the processor 154 to control the operation and function of the medical apparatus 100. The computer memory 160 is shown as containing an image reconstruction module 192. The image reconstruction module 192 enables the processor 154 to reconstruct the magnetic resonance image 166 from the magnetic resonance data 164. The computer memory 160 is further shown as containing an image registration module 194 which enables the processor 154 to register anatomical landmarks of the subject 136 identified in the treatment plan 168 with the magnetic resonance image 166.

The image registration module 194 may also be used in other examples for other types of image processing such as identifying the location of a fiducial marker within the radiation detectors 144. The computer memory 160 is further shown as containing the control command generation module 196. The control command generation module 196 contains computer executable code which enables the processor 154 to drive the radiation therapy device control commands using the magnetic resonance data 164 and/or the magnetic resonance image 166 and the treatment plan 168. In some examples the control command generation module 196 may also enable the processor 154 to modify the radiation therapy device control commands 172 on the fly in response to a determination of the spatially dependent radiation dose 182 and/or the three-dimensional radiation path 184. It may also be able to identify the radiation therapy device control commands in response to the time-dependent radiation beam path 176 and/or the time-dependent radiation beam intensity 178. The computer memory 160 is further shown as containing a beam path intensity determination module 198 which is able to calculate the time-dependent radiation beam path and/or time-dependent radiation beam intensity 178 using the radiation detection data 174.

The computer memory 160 is further shown as containing a radiation model module 199. The radiation model module 199 may for instance enable the processor 154 to model the radiation absorption model of the subject 180 using the magnetic resonance image 166 and/or calculate the spatially dependent radiation dose 182 and/or calculate the three-dimensional radiation path 184. The contents of the computer storage 158 and the computer memory 160 may be in some examples exchanged or duplicated within both of them. Not all of the data or software modules shown within the computer storage 158 or the computer memory 160 is present in all examples. It is understood that various features of the medical apparatus 100 may be removed or deleted in various examples.

Figure 2:
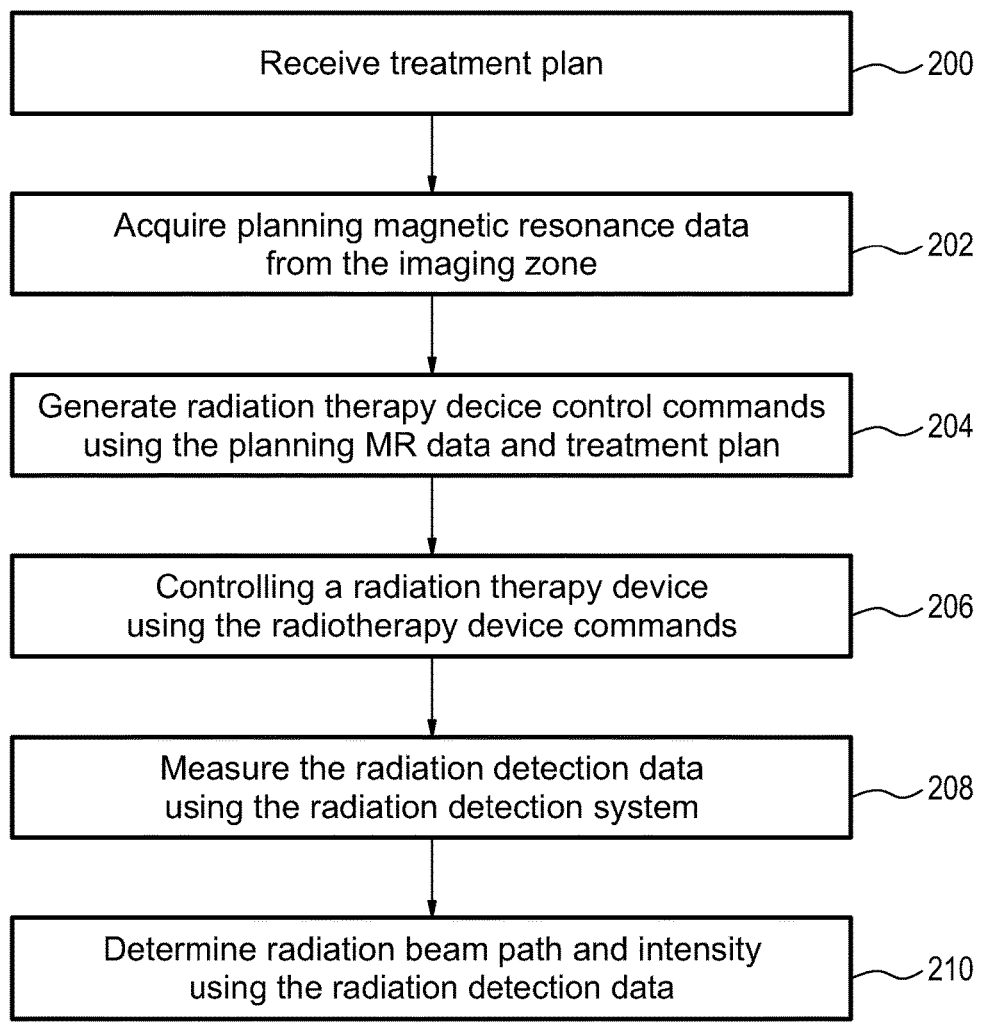
FIG. 2 shows a flow chart which illustrates an example of a method.

FIG. 2 shows a flowchart which illustrates an example of a method for operating the medical apparatus 100. First in step 200 a treatment plan 168 is received which is descriptive of the irradiation of a target zone 138 in the subject 136. The subject support is operable 134 for positioning the subject 136 such that the target volume 139 within the target zone 138 is not shown in FIG. 1 but the medical apparatus may comprise a system for moving or positioning the subject support 134. Next in step 202 planning magnetic resonance data 164 which is also referred to as magnetic resonance data 164 in FIG. 1 may be acquired from the imaging zone 132 using the magnetic resonance imaging system 104. For instance the pulse sequence 162 may be used for controlling the magnetic resonance imaging system to achieve this.

Next in step 204 radiation therapy device control commands 172 are generated or calculated using the planning magnetic resonance data 164 and the treatment plan 168. There may be intermediate steps such as generating the magnetic resonance image 166 and/or registering the magnetic resonance image to the treatment plan 168. Next in step 206 the target zone 139 is irradiated by controlling the radiation therapy device 102 using the radiation therapy device control commands 172. Next in step 208 the radiation detection data 174 is measured using the radiation detection system 146 during the irradiation of the target zone 139. Finally in step 210 a time-dependent radiation beam path 176 and a time-dependent radiation beam intensity 178 is determined using the radiation detection data 174. The time-dependent radiation beam path 176 is descriptive of a path of the radiation beam 142 through the subject 136 as a function of time. The time-dependent radiation beam intensity 178 is descriptive of the intensity of the radiation beam in the subject 136 as a function of time. If a radiation absorption model of the subject 136 has not been determined then the beam path 176 and corresponding intensities 178 are the values that are known at the two services defined by the detectors 144.

Figure 3:
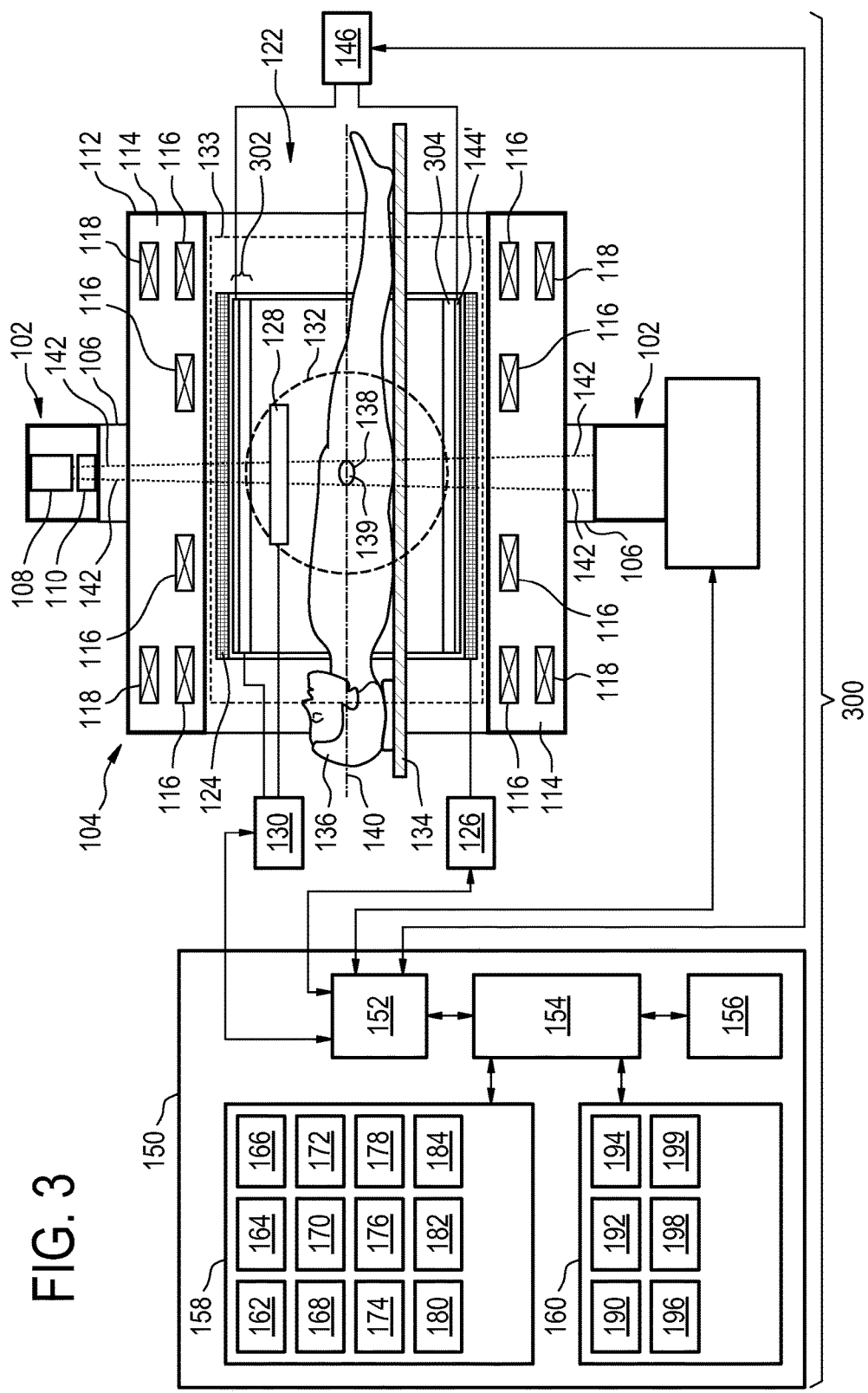
FIG. 3 illustrates a further example of a medical apparatus.

FIG. 3 shows a further example of medical apparatus 300. In this example within the bore of the magnet 122 is mounted a body coil 302. The body coil 302 may for instance be a transmit, receive, or a transmit and receive coil for acquiring or generating RF pulses during the acquisition of the magnetic resonance data 164. It is shown as being connected to the receiver 130. The radio-frequency coil 128 is still shown in FIG. 3. The radio-frequency coil 128 may be an additional coil 128 which is used to for the acquisition of magnetic resonance data or it may also be a coil 128 that is used in conjunction with the body coil 302. For example in some examples the coil 128 may be a surface coil 128 used to excite nuclear spins within the imaging zone 132 and the body coil 302 is used to measure the magnetic resonance data 164. This is however purely an example and not intended to be limiting.

The body coil 302 is mounted within the gradient coils 124. The body coil 302 comprises an inner layer which contains the coil elements 304. Outside of the coil elements 304 is a radio-frequency shield 144 to prevent the body coil 302 from interfering with the function of the gradients 124 and/or the magnet 112. In this case the radio-frequency shield 144 incorporates an array of solid state radiation detectors. Use of such radiation shields 144 is known and often times there are slits or discontinuities in the metallic or conductive surface which is used to block radio-frequency but allows magnetic field from the magnet 112 or the gradient coils 124 to pass through it. The breaks in the metal may for instance have small islands which are arranged in a pseudo random factor such that it does not interfere with the acquisition of magnetic resonance data 164 or the radiation beam 142.

Portal imaging is normally used for monitoring LINAC irradiation by fluoroscopic imaging of the MV (megavoltage) beam once it has passed through the patient. The portal image has poor image quality and little contrast compared to kV imaging, but unlike kV imaging, it does not introduce extra, non-therapeutic radiation, to the patient. The portal images can be used to monitor patient motion and positioning within the LINAC device.

Portal imaging in MR Linac devices is difficult to achieve with conventional techniques: A conventional EPID (electronic portal imaging device) is located on the other side of the rotating gantry and the gantry needs to be large to incorporate the MR imager within the gantry. The large distance from the beam source to the EPID results in poor signal to noise and small field of view in the area of interest (in the middle of the gantry).

Portal imaging is, however, very important safety mechanism as it ties MR images to portal CT/fluoroscopy images: same structures can be imaged with both modalities concurrently. Gross errors in patient position can be detected.

Figure 4:
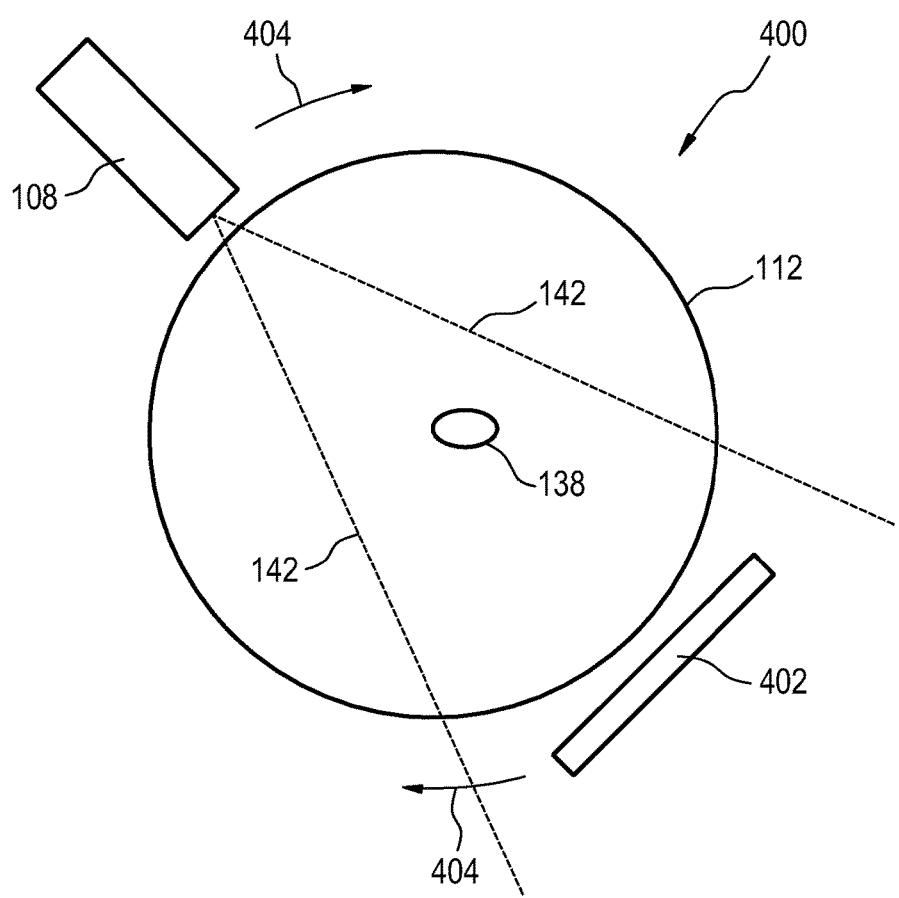
FIG. 4 illustrates a further example of a medical apparatus.

FIG. 4 shows an example of a medical apparatus 400. The beam source 108 in this example is directed towards an electronic portal imaging device 402. The electronic portal imaging device 402 is located outside of the magnet 112. The radiation beam 142 from the radiation source 108 irradiates the target zone 138. The electronic portal imaging device 402 is mounted opposite of the radiation source 108 and is able to make a crude image of a subject within the magnet 112. The arrows 404 indicate that both the source 108 and the portal imager 402 rotate together around the magnet 112. Such an electronic portal imaging device 402 may be incorporated into the other examples within this document.

Examples herein may describe a portal imager/radiation detector device that is integrated with/takes into account the stationary transmission coil of an MR scanner. E.g., the elements that detect radiation are to be integrated into the RF-shield of the transmission coil, so that the detector elements are outside the powerful B1 RF fields, but as close as possible to the target being MR-scanned and LINAC-irradiated.

In one example, a thin detector sheet with negligible eddy currents is rotated together with the gantry.

In one example, the detector sheet is stationary, but covers substantial part/whole 360 degrees of the rotation. Covering of a substantial part of the rotation of the gantry is preferably coverage of a total angle of more than 180 degrees, more preferably it is coverage of a total angle of more than 270 degrees and even more preferably it is coverage of a total angle of more than 320 degrees. It should hereby be noted that the angle is not necessarily contiguous, but could e.g. also be formed by a total of smaller detectors (e.g. islets), each covering a smaller angle. This latter embodiment results in part of the detectors being temporally deprived of the tangential signal, but simplifies the construction and provides a thinner sheet. It also provides an opportunity to measure radiation before it enters the patient and after the radiation has interacted with the patient.

In one example, the detector sheet is divided into sheet islets (e.g., pseudo-random pattern to prevent RF interference/portal imaging artifacts), which are connected either non-galvanically (e.g., optically or wirelessly at non-interfering frequency), or via galvanic filters, to each other and/or to the central unit, which combines the partial signals from several islets to a larger image/spatial detection area.

Figure 5:
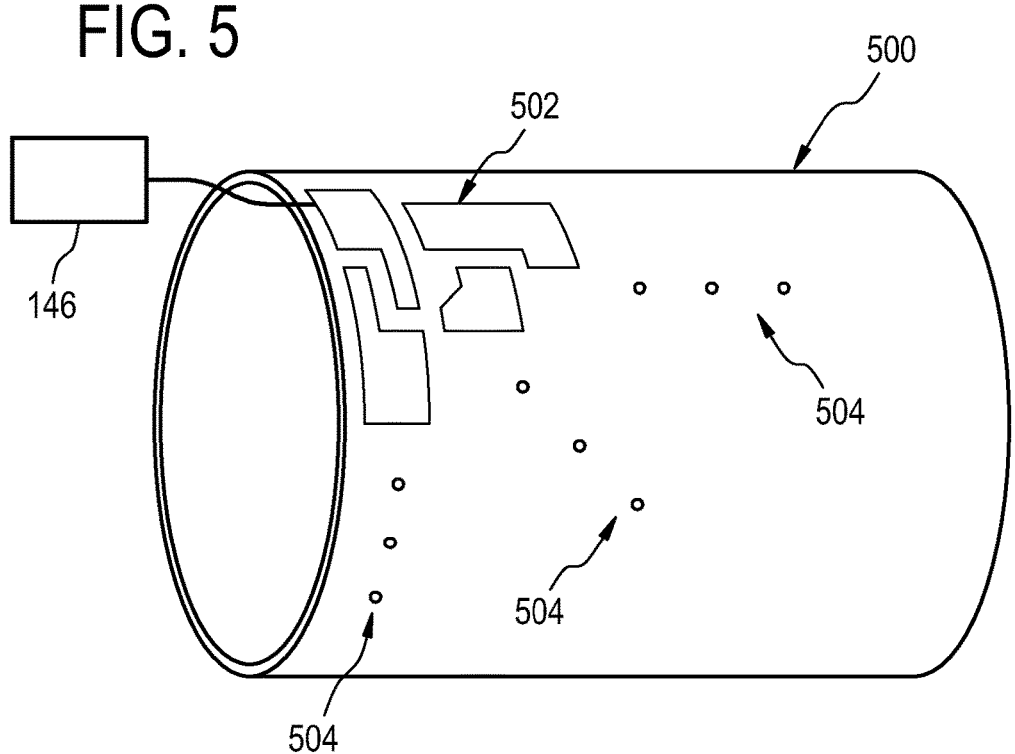
FIG. 5 illustrates an example of a radiation detector.

FIG. 5 shows an example of a radio-frequency shield 500 which may be incorporated into the body coil 302 of FIG. 3. There is a pseudo random pattern 502 of conductors which contain solid state radiation detectors. A portion of the pattern is indicated by 502. The dots 504 indicate that a pseudo random pattern is distributed around the whole surface of the radio-frequency shield 500.

In one embodiment, the islets form part of the RF shielding structure by offering mechanical support and/or low conductance paths at transmission frequencies, which can be further used to design the band-stop resonant circuits typically found in such shields. In one embodiment, the islets are small enough to allow integration with receiver coils or bore within the transmission coil, without causing RF interference with transmission/receiver coils.

In one embodiment, the detectors are actively shielded by synchronizing gradient and RF events with detection: the detectors are actively shielded to act transparent to the RF and gradient fields, hibernate during high interference signaling from the MR scanner, and resume operation after the MR events are over.

The transmission coil or body coil is typically a birdcage coil (QBC or quadrature body coil), which forms a cylinder within the magnet bore. The shape makes it possible to drape a thin sheet of detectors around the cylinder such as is shown in FIG. 6.

Figure 6:
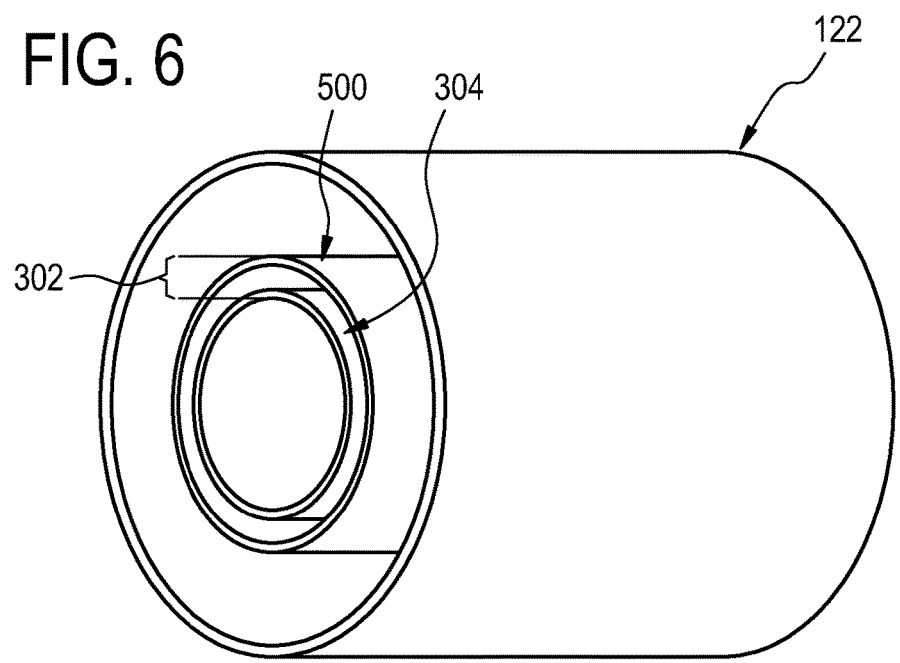
FIG. 6 illustrates an example of a body coil with an integrated radiation detector.

FIG. 6 shows a figure which contains a coil 304 and a radio-frequency shield 500 within the bore 122 of a magnet as is shown in FIG. 3. The coil elements 304 and the radio-frequency shield 500 make up the body coil 302.

QBC requires a high-Q RF shield to prevent the gradient coils/magnet bore from loading the coil at high transmission frequencies, while still allowing the low-frequency gradient fields to pass through the RF shield without eddy currents within the field. By dividing the detector in islets, the eddy currents are prevented. If the detectors are outside the RF-shielding elements (typically discrete components), the loading effect from the detector in negligible—one can do without the islets design altogether if thin sheet material does not introduce large eddy currents. If the islets are part of the RF shield, the foil copper can be used to form paths for RF-shielding currents and to introduce areas of low RF power for sensitive detector electronics integrated into the foil.

The islet communication can be non-galvanic: 2.4 GHz wireless transmission, optical. For galvanic communication, band-stop around transmission RF frequencies and high pass to prevent eddy currents at low frequencies are needed.

Active shielding: large interfering structures within the radiation detector are broken with PIN-diodes/FET transistors, similarly with coil preamplifiers.

Figure 7:
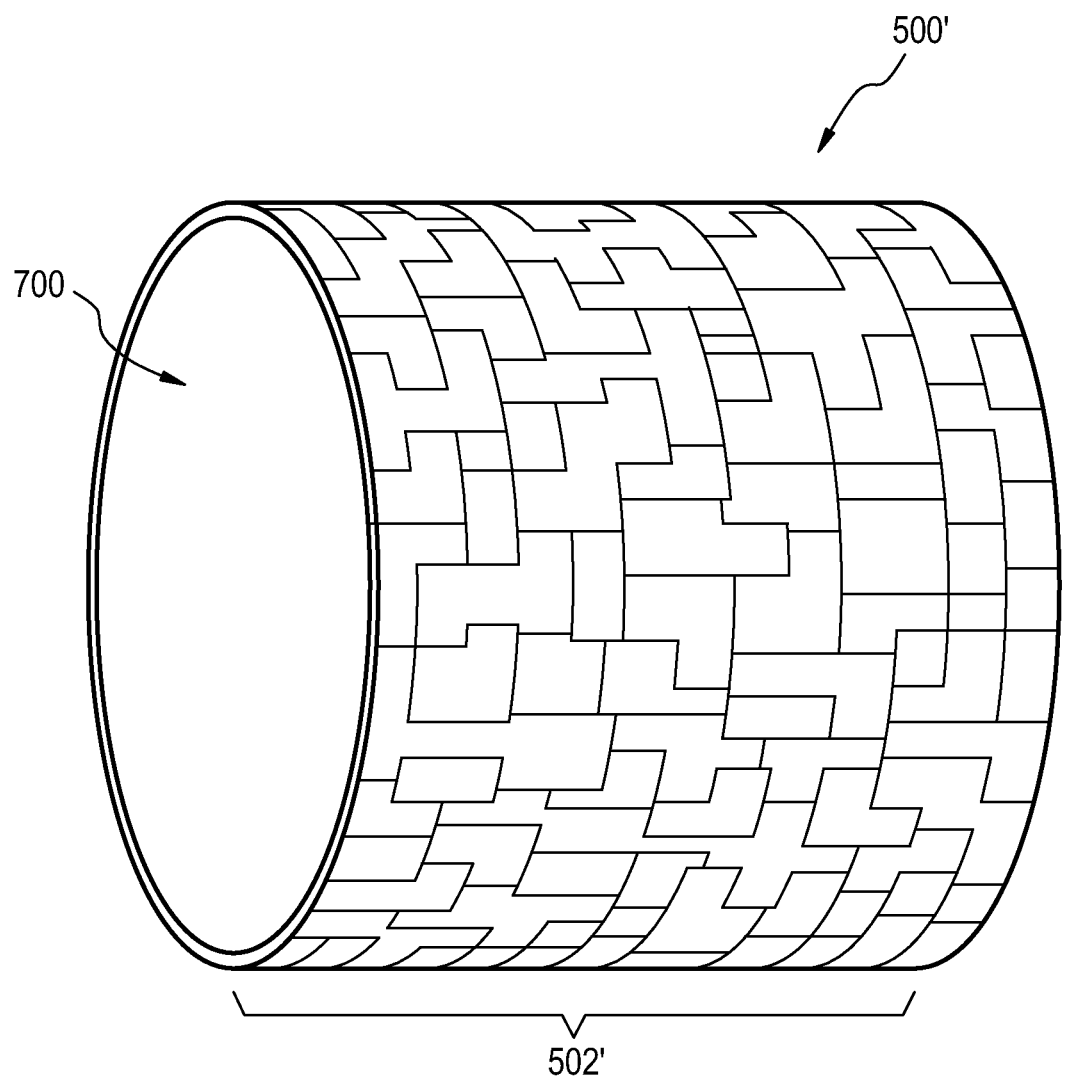
FIG. 7 illustrates an example of a radiation detector.

FIG. 7 shows a further example of a radio-frequency shield 500'. The arrow 700 indicates the location of a hollow portion 700 where the coil elements 304 may be placed. On the surface of the radio-frequency shield 500 is a pseudo random pattern 502' of conductive materials arranged in a tile-like and pseudo random fashion. Semi-conductor radiation detectors may be incorporated throughout the metallic portions 502' arranged in a pseudo random fashion.

Figure 8:
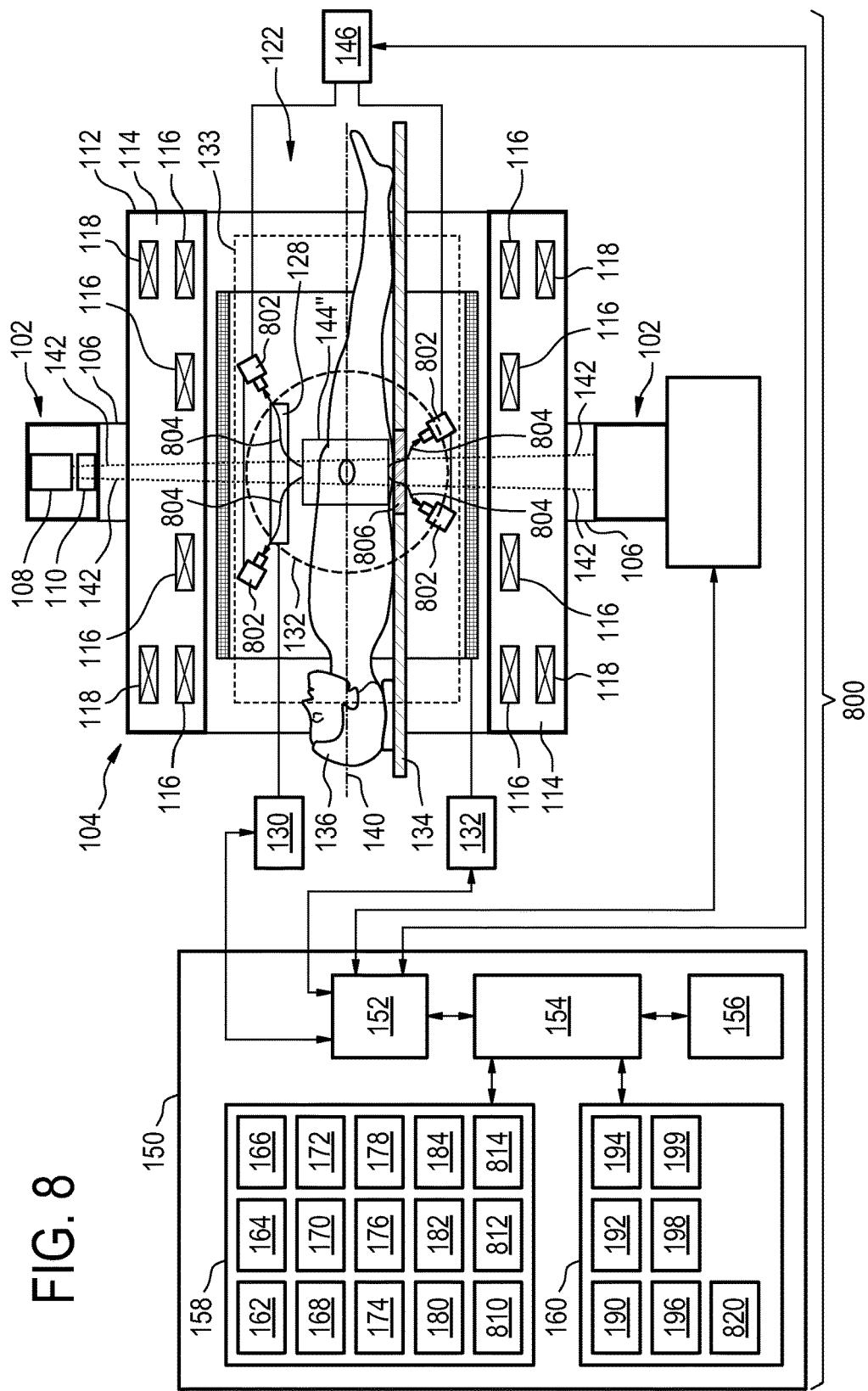
FIG. 8 illustrates a further example of a medical apparatus.

FIG. 8 shows a further example of a medical apparatus 800. The medical apparatus 800 is similar to that shown in FIG. 1. However in this case, the radiation detection system 146 also incorporates a number of cameras 802 for detecting light emissions 804 from a scintillator film 144" which is wrapped around the subject 136. The light emissions 804 are shown as going through the radio-frequency coil 128. In some cases the radio-frequency coil 128 may have transparent regions or regions through which light may pass or the radio-frequency coil 128 may be positioned such that it does not interfere with light emissions 804 reaching the cameras 802. Some examples may also incorporate a transparent portion 806 in the subject support 134 such that light emissions 804 may pass through the subject support 134 to additional cameras 802. A number of cameras 802 are aimed at the surfaces 144" defined by the scintillator film 144". Use of multiple cameras enables the determination of the precise location of light emissions 804.

Figure 9:
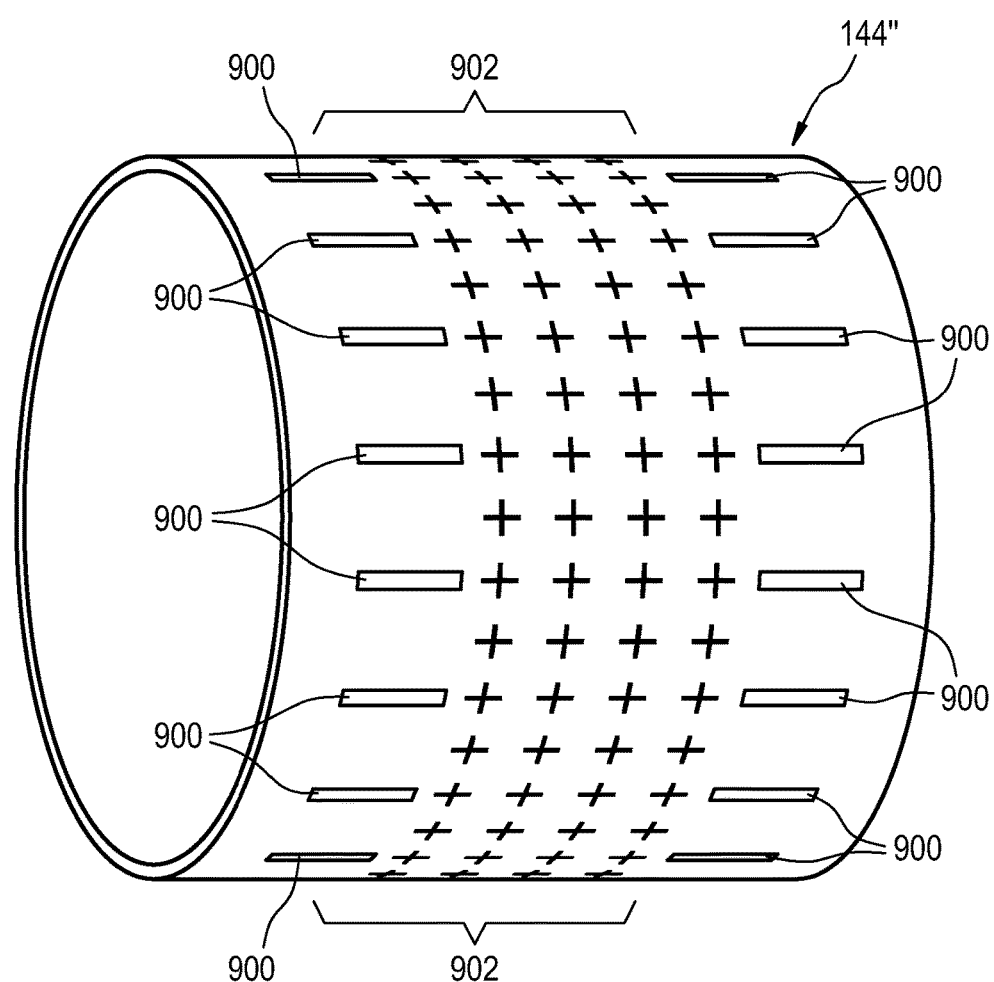
FIG. 9 illustrates an example of a scintillator film.

FIG. 9 is used to further illustrate one example of a scintillator film 144" such as could be used in the example shown in FIG. 8. The scintillator film 144" is shown as being wrapped in the shape of a drum. The subject can be placed within the scintillator film 144". There are a number of fiducial markers 900 which are mounted on the surface or within or underneath the scintillator film 144". This enables the location of the surface to be determined using the magnetic resonance image 166 or the magnetic resonance data 164. There are also a number of optical markers 902 which may be machine-readable markers. The same marker may be imaged by multiple cameras 802. Knowledge of how the cameras 802 are positioned, or a calibration, relative to the radiation therapy device 102 the magnetic resonance imaging system 104 enables a determination of the position of the surface of the scintillator film 144" to be determined.

In other examples the scintillator film 144" may be a sheet which is laid on top of and a second sheet is laid underneath the subject 136. The scintillator film may be wrapped and then snapped or clipped such that it surrounds the subject 136. In other instances the subject may wear a garment which has scintillator films attached to it. In other embodiments the scintillator film may be sections of scintillator film which are operable for being attached to the garment of a subject 136. When using the medical apparatus 800 of FIG. 8 the location of the fiducial markers 810 may be determined from the magnetic resonance data 164 or the magnetic resonance image 166 using the image registration module 194. Computer storage 158 is shown as containing the location of the fiducial markers 810.

The computer storage 158 is also shown as containing initial images 812. Initial images 812 are images taken by the cameras 802 of the surface of the scintillator film 144". These are used to measure the location of the optical markers 902 for determination of the surface position. The location of the surface 814 may for instance be calculated in an image processing module 820. The location of the surface 814 is shown as being stored by the storage 158 and the image processing module 820 is shown as being stored in the computer memory 160.

Examples may provide a way to directly measure the spatial distribution of the deposited dose and to map this information to the MR image coordinates.

The measurement is performed optically by monitoring the light emitted by a scintillator foil wound around the patient's body.

Examples may provide a way to check whether the applied dose distribution is consistent with the treatment plan and it can be used to shut down the radiation system if any deviation from the plan is detected. This can further be applied to calibrate and align the radiation source.

Components of some examples: Scintillator foils made of plastic scintillators have been commercially available for many years. The image acquisition and processing required for this invention has become possible with today's sensitive CCD camera chips and real-time computing capabilities.

Currently, the MR-Linac system offers no way to monitor the deposited dose by direct measurement. While the organs in the patient's body can be imaged in real time, treatment relies only on accurate beam alignment and calculations, but there is no feedback system.

Examples may provide a way to directly measure the spatial distribution of the deposited dose and to map this information to the MR image coordinates. Examples may offers a way to check whether the applied dose distribution is consistent with the treatment plan and it can be used to shut down the radiation system if any deviation from the plan is detected.

The main elements of some examples are:
1. a scintillator foil surrounding and attached to the patient's body,
2. markers visible both optically and by MR measurement, attached to the scintillator foil
3. an optical imaging system consisting of one or several cameras to detect both scintillation and markers,
4. a feedback mechanism which compares the measured dose distribution with the original treatment plan and shuts down the radiation source if any deviation is detected.

Examples may be used within an MR-Linac system, which provides both the therapeutic radiation and the real-time MR imaging capabilities.

A sketch of the example of FIG. 8 is shown in FIGS. 10 and 11. FIG. 10 shows a cross-sectional view of some of the components of the example shown in FIG. 8. The medical apparatus 800 is shown with the magnetic resonance imaging system 104 and the radiation therapy device 102. Not all components are shown in FIG. 10. The radiation source 108 is rotated by the gantry along the path indicated by the arrows 1000. The cameras 802 are positioned such that they can view the surface of the scintillator foil 144". Fiducial markers 900 can be detected by the magnetic resonance imaging. They may at the same time serve as optical markers detectible by the cameras 802. The radiation beam 142 generated by the radiation source 108 is shown as penetrating the scintillator foil 144" at two locations.

FIG. 11 is a view of the subject 136 being irradiated by the radiation beam 142. The radiation beam 142 is shown as passing through the subject 136. The scintillator foil 144" is wrapped around the subject 136. The scintillator foil 144" includes several fiducial markers 900. At the points where the radiation beam 142 penetrates the scintillator foil 144" light is generate and there are light emissions 804. Cameras 802 are positioned to measure the intensity and location of the light emissions 804. A previous calibration may be used with the combination of several cameras 802 to indicate the position and intensity of the light emissions 804 thereby indicating the position and intensity of the radiation 142 as a function of time.

A thin foil of a plastic scintillator material, mounted on a bendable substrate, is wound around the part of the patient's body to be treated by radiation. The gamma beam used for radiation therapy is produced by a linear accelerator on a rotating gantry. A multi-leaf collimator (MLC), rotating with the radiation source, is used to shape the beam cross section. A measurement of the shape and position of the beam is performed optically by monitoring the light emitted by the scintillator foil wound around the patient's body. To this aim, several optical cameras are placed at different positions within the MR scanner in such a way that every point on the scintillator surface can be seen by at least two cameras. In this way, a stereo picture can be taken and the beam entry or exit regions can be measured in 3d space. Optional markers on the scintillator which are visible both in the optical and in the MR image can be used to map the coordinate system of the cameras and the MR scanner to one another.

Plastic scintillators typically emit light at a wavelength around 450 nm. To ensure that even low light levels can be measured reliably without too much background signal, spectral filters can be placed in front of the cameras and at the same time the ambient lighting in the treatment room can be designed such that there are no spectral contributions in respective range (e.g. using LED lighting).

The thickness of the scintillator foil is chosen such that the light emission is sufficient to be detected by the cameras and there is still no significant loss of gamma radiation power.

Camera images from below the patient can be taken through an optically transparent window or hole in the patient support beneath the treatment region.

The gamma radiation passes through the scintillator foil, then through the patient's body, then again through the scintillator foil on the opposite side. When passing through the scintillator, a small fraction of the energy is converted to visible light so that the cross section of the gamma beam becomes visible on the scintillator foil surface.

By measuring the shape of the gamma radiation beam at the entry and the exit regions on the scintillator foil simultaneously, the exact propagation direction and spatial distribution within the patient's body can be determined.

The co-registration of both radiation distribution and MR image data, either by markers or by known alignment of the optical cameras, then allows mapping the dose distribution to the image data.

The resulting information can be used for
manually checking the dose distribution after the treatment,
automatically comparing the measured dose distribution with the initial treatment plan and shutting down the radiation source for security reasons whenever a deviation from the plan is detected.

Examples may also be used to calibration or regular checks of the gamma beam alignment by scanning a phantom instead of the patient.

Depending on the optical access to the scintillator and the number of cameras installed in the system, measurements may not be possible for all beam angles.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 medical apparatus
102 radiation therapy device
104 magnetic resonance imaging system
106 gantry
108 radiotherapy source
110 collimator
112 magnet
114 cryostat
116 superconducting coil
118 superconducting shield coil
122 bore
124 magnetic field gradient coil
126 magnetic field gradient coil power supply
128 radio frequency coil
130 transceiver
132 imaging zone
133 main field region
134 subject support
136 subject
138 target zone
139 target volume
140 rotational axis
142 radiation beam
144 radiation detector
144' semiconductor radiation detector
144" scintillator film
146 radiation detection system
150 computer system
152 hardware interface
154 processor
156 user interface
158 computer storage
160 computer memory
162 pulse sequence
164 magnetic resonance data
166 magnetic resonance image
168 treatment plan
170 registration between image 166 and treatment plan 172 radiation therapy device control commands
174 radiation detection data
176 time dependent radiation beam path
178 time dependent radiation beam intensity
180 radiation absorption model of subject
182 spatially dependent radiation dose
184 three dimensional radiation path
190 control module
192 image reconstruction module
194 image registration module
196 control command generation module (also mention real time control)
198 beam path and intensity determination module
199 radiation model module (dose, model of subject, rad path)
300 medical apparatus
302 body coil
304 radio frequency shield
306 coil elements
400 medical apparatus
402 electronic portal imaging device
404 rotation of gantry
500 radio frequency shield
500' radio frequency shield
502 pseudo random design
502' pseudo random design
504 dots indicate continuation of pattern
700 hollow portion
800 medical apparatus
802 camera
804 light emission
806 transparent portion
810 location of fiducial markers
812 initial images
814 location of surface
820 image processing module
900 fiducial markers
902 optical position markers
1000 direction of travel

The invention claimed is:

1. A medical apparatus comprising:
a magnetic resonance imaging system configured to acquire magnetic resonance data from a subject within an imaging zone, wherein the magnetic resonance imaging system comprises a main magnet configured to generate a main magnetic field with a main field region, wherein the imaging zone is within the main field region;
a radiation therapy device comprising a gantry and a radiation source, wherein the gantry is configured to rotate the radiation source about a rotational axis, wherein the radiation source is configured to generate a radiation beam directed at the rotational axis, wherein the radiation source is configured to direct the radiation beam towards a target volume, wherein the rotational axis intersects the target volume, wherein the target volume is within the imaging zone;
a radiation detection system including at least one radiation detector covering at least 180° of a rotation angle of the gantry and configured to measure radiation detection data descriptive of a path and an intensity of the radiation beam at an intersection of the radiation beam with at least one surface surrounding the subject using the at least one radiation detector, wherein the at least one radiation detector is configured to be placed within the main field region and measure the radiation data when the radiation detector is placed within the main magnetic field, wherein the at least one radiation detector includes a scintillator film configured to emit light in response to being irradiated by the radiation beam, the scintillator film being disposed in the main magnetic field and extending at least 180° around the imaging zone wherein the radiation detection system further includes fiducial markers mounted with the scintillator film and optical cameras mounted to generate images of the light emitted by the scintillator film;
a subject support configured to support the subject;
a memory configured to store machine executable instructions;
a processor configured to control the medical apparatus, wherein execution of the instructions causes the processor to:
receive a treatment plan descriptive of irradiation of a target zone within the subject, wherein the subject support is further configured to position the target volume within the target zone,
acquire the magnetic resonance data from the imaging zone using the magnetic resonance imaging system;
generate radiation therapy device control commands using the magnetic resonance data and the treatment plan;
irradiate the target zone by controlling the radiation therapy device using the radiation therapy device control commands;
measure the radiation detection data during irradiation of the target zone using the radiation detection system; and
determine a time dependent radiation beam path and a time dependent radiation beam intensity using the radiation detection data, wherein the time dependent radiation beam path is descriptive of the path of the radiation beam through the subject as a function of time, wherein the time dependent radiation beam intensity is descriptive of the intensity of the radiation beam in the subject as a function of time.

2. The medical apparatus of claim 1, wherein execution of the instructions further causes the processor to calculate a spatially dependent radiation dose of the subject using the time dependent radiation beam path and the time dependent radiation beam intensity using the radiation detection data.

3. The medical apparatus of claim 1, wherein execution of the instructions further causes the processor to calculate a three dimensional radiation path through the subject using the time dependent radiation beam path and the time dependent radiation beam intensity using the radiation detection data.

4. The medical apparatus of claim 1, wherein execution of the instructions further causes the processor to modify the radiation therapy device control commands using the time dependent radiation beam path, the time dependent radiation beam intensity, the magnetic resonance data, and the treatment plan.

5. The medical apparatus of claim 1, wherein the optical cameras are attached to the magnet and directed towards the imaging zone, wherein the memory further contains camera orientation data descriptive of the location and orientation of the multiple cameras relative to the magnet, wherein the at least one scintillator film is configured to emit light of a predetermined frequency spectrum in response to being irradiated by the radiation beam, wherein the at least one scintillator film comprises optical position markers,
wherein execution of the instructions further causes the processor to:

identify the location of the fiducial markers in the magnetic resonance data;
measure initial images of the at least one scintillator film with the multiple cameras;
identify the location of the at least one surface surrounding the subject by identifying the location of the optical position markers in the initial images and using the location of the fiducial markers; and
acquire the radiation detection data by detecting the light of the predetermined frequency spectrum during irradiation of the target zone.

6. The medical apparatus of claim 5, wherein the subject support comprises a transparent portion, wherein a portion of the optical cameras are operable for observing the at least one scintillator film through the transparent portion.

7. The medical apparatus of claim 5, wherein the at least one scintillator film is operable to be wrapped around the subject.

8. The medical apparatus of claim 5, wherein the at least one scintillator film is operable to be attached to a garment.

9. The medical apparatus of claim 1, wherein the radiation therapy device is any one of the following: a LINAC system, an x-ray system, a charged particle therapy system, and a gamma radiation therapy system.

10. A medical apparatus comprising:
a magnetic resonance imaging system configured to acquire magnetic resonance data from a subject within an imaging zone, wherein the magnetic resonance imaging system comprises a main magnet configured to generate a main magnetic field in a main field region, wherein the imaging zone is within the main field region;
a radiation therapy device comprising a gantry and a radiation source, wherein the gantry is configured to rotate the radiation source about a rotational axis, wherein the radiation source is configured to generate a radiation beam directed at the rotational axis, wherein the radiation source is configured to direct the radiation beam towards a target volume, wherein the rotational axis intersects the target volume, wherein the target volume is within the imaging zone;
a radiation detection system including at least one radiation detector covering at least 180° of a rotation angle of the gantry and configured to measure radiation detection data descriptive of a path and an intensity of the radiation beam at an intersection of the radiation beam with at least one surface surrounding the subject using the at least one radiation detector, wherein the at least one radiation detector is configured to be placed within the main field region and measure the radiation data when the radiation detector is placed within the main magnetic field, wherein the medical apparatus comprises the radiation detector, wherein the radiation detector comprises an array of solid state radiation detectors;
a subject support configured to support the subject;
a memory configured to store machine executable instructions;
a processor configured to control the medical apparatus, wherein execution of the instructions causes the processor to:
receive a treatment plan descriptive of irradiation of a target zone within the subject, wherein the subject support is further configured to position the target volume within the target zone,
acquire the magnetic resonance data from the imaging zone using the magnetic resonance imaging system;
generate radiation therapy device control commands using the magnetic resonance data and the treatment plan;
irradiate the target zone by controlling the radiation therapy device using the radiation therapy device control commands;
measure the radiation detection data during irradiation of the target zone using the radiation detection system; and
determine a time dependent radiation beam path and a time dependent radiation beam intensity using the radiation detection data, wherein the time dependent radiation beam path is descriptive of the path of the radiation beam through the subject as a function of time, wherein the time dependent radiation beam intensity is descriptive of the intensity of the radiation beam in the subject as a function of time.

11. The medical apparatus of claim 10, wherein the solid state radiation detectors are arranged in a pseudorandom pattern in the array.

12. A medical apparatus comprising:
a magnetic resonance imaging system including a main magnet configured to generate a main magnetic field in an imaging zone and a body coil configured to measure magnetic resonance data and/or transmit radio frequency power into the imaging zone and a radio frequency shield disposed between the body coil and the main magnet;
a radiation therapy device configured to rotate a radiation beam directed at an axis of rotation;
a radiation detection system including a radiation detector covering at least 180° around a rotation angle of the radiation beam around the axis of rotation, the radiation detector included with the radio frequency shield and being configured to measure radiation detection data descriptive of a path and an intensity of the radiation beam at an intersection of the radiation beam with the radiation detector;
a subject support configured to position a target volume of a subject in the imaging zone intersecting the axis of rotation;
a processor configured to:
receive a treatment plan descriptive of irradiation of a target zone of the subject,
receive the magnetic resonance data from the body coil,
generate radiation therapy device control commands using the magnetic resonance data and the treatment plan,
irradiate the target zone by controlling the radiation therapy device using the radiation therapy device control commands,
measure the radiation detection data during irradiation of the target zone using the radiation detector in the main magnetic field; and
determine a time dependent radiation beam path and a time dependent radiation beam intensity using the radiation detection data, wherein the time dependent radiation beam path is descriptive of the path of the radiation beam through the subject as a function of time, wherein the time dependent radiation beam intensity is descriptive of the intensity of the radiation beam in the subject as a function of time.

13. A non-transitory computer readable medium comprising machine executable instructions for execution by a processor controlling a medical apparatus, wherein the medical apparatus comprises a magnetic resonance imaging system configured to acquire magnetic resonance data from a subject within an imaging zone, wherein the magnetic resonance imaging system comprises a main magnet for generating a magnetic field with a main field region, wherein the imaging zone is within the main field region, wherein the medical apparatus further comprises a radiation therapy device comprising a gantry and a radiation source, wherein the gantry is configured to rotate the radiation source about a rotational axis, wherein the radiation source is configured to generate a radiation beam directed at the rotational axis, wherein the radiation source is configured to direct the radiation beam towards a target volume, wherein the rotational axis intersects the target volume, wherein the target volume is within the imaging zone, wherein the medical apparatus further comprises a radiation detection system including at least one radiation detector covering at least 180° of a rotation angle of the gantry and configured to measure radiation detection data descriptive of a path and an intensity of the radiation beam at an intersection of the radiation beam with at least one surface surrounding the subject using the at least one radiation detector, wherein the at least one radiation detector is configured to be placed within the main field region and measure the radiation data when the radiation detector is placed within the main magnetic field, wherein the medical apparatus comprises the radiation detector, wherein the radiation detector comprises an array of solid state radiation detectors, wherein the medical apparatus further comprises a subject support configured to support the subject, wherein execution of the instructions causes the processor to:
  receive a treatment plan descriptive of irradiation of a target zone within the subject and control the subject support to position the target volume within the target zone;
  acquire the magnetic resonance data from the imaging zone using the magnetic resonance imaging system;
  generate radiation therapy device control commands using the magnetic resonance data and the treatment plan;
  control the radiation source to irradiate the target zone using the radiation therapy device control commands;
  measure the radiation detection data during irradiation of the target zone using the radiation detection system; and
  determine a time dependent radiation beam path and a time dependent radiation beam intensity using the radiation detection data, wherein the time dependent radiation beam path is descriptive of the path of the radiation beam through the subject as a function of time, wherein the time dependent radiation beam intensity is descriptive of the intensity of the radiation beam in the subject as a function of time.

14. A method of operating a medical apparatus, wherein the medical apparatus comprises a magnetic resonance imaging system configured to acquire magnetic resonance data from a subject within an imaging zone, wherein the magnetic resonance imaging system comprises a main magnet configured to generate a magnetic field in a main field region and a body coil configured to measure magnetic resonance data and/or transmit radio frequency power into the imaging zone and a radio frequency shield disposed between the body coil and the main magnet, wherein the imaging zone is within the main field region, wherein the medical apparatus further comprises a radiation therapy device comprising a gantry and a radiation source, wherein the gantry is configured to rotate the radiation source about a rotational axis, wherein the radiation source is configured to generate a radiation beam directed at the rotational axis, wherein the radiation source is configured to direct the radiation beam towards a target volume, wherein the rotational axis intersects the target volume, wherein the target volume is within the imaging zone, wherein the medical apparatus further comprises a radiation detection system including a radiation detector covering at least 180° around a rotation angle of the radiation beam around the rotational axis, the radiation detector included with the radio frequency shield and being configured to measure radiation detection data descriptive of a path and an intensity of the radiation beam at an intersection of the radiation beam with the radiation detector, wherein the medical apparatus further comprises a subject support configured to support the subject, wherein the method comprises the steps of:
  receiving a treatment plan descriptive of irradiation of a target zone within the subject, wherein the subject support is further operable for positioning the target volume within the target zone;
  acquiring the magnetic resonance data from the imaging zone using the magnetic resonance imaging system;
  generating radiation therapy device control commands using the magnetic resonance data and the treatment plan;
  controlling the radiation therapy device using the radiation therapy device control commands for irradiating the target zone;
  measuring the radiation detection data during irradiation of the target zone using the radiation detection system; and
  determining a time dependent radiation beam path and a time dependent radiation beam intensity using the radiation detection data, wherein the time dependent radiation beam path is descriptive of the path of the radiation beam through the subject as a function of time, wherein the time dependent radiation beam intensity is descriptive of the intensity of the radiation beam in the subject as a function of time.

15. A radiation therapy method comprising:
  acquiring magnetic resonance data from a subject in an imaging zone;
  generating a main magnetic field in the imaging zone with a main magnet;
  rotating a radiation therapy source about a rotation axis;
  generating a radiation beam directed toward a rotational axis with the radiation source;
  positioning a subject such that a target volume of the subject and the rotational axis are disposed in the imaging zone;
  with a radiation detector extending at least 180° around the rotational axis, measuring therapy radiation data descriptive of a path and an intensity of the radiation beam;
  wherein the radiation detector includes a scintillator film configured to emit light in response to being irradiated by the radiation beam, the scintillator film being disposed in the main magnetic field and extending at least 180° around the imaging zone;
  receiving a treatment plan descriptive of irradiation of the target volume;
  generating radiation beam rotation and intensity control commands using the magnetic resonance data and the treatment plan;
  controlling the radiation therapy source with the control commands to irradiate the target volume;
  measuring the therapy radiation data during irradiation of the target volume using the at least one radiation detector;

determining a time-dependent radiation beam path and a time-dependent radiation beam intensity using fiducial markers mounted with the scintillator film, optical cameras mounted to generate images of the light emitted by the scintillator film, and the therapy radiation data, wherein the time-dependent radiation beam path is descriptive of the radiation beam through the subject as a function of time and wherein the time-dependent radiation beam intensity is descriptive of the intensity of the radiation beam in the subject as a function of time.

* * * * *